(12) United States Patent
Albright et al.

(10) Patent No.: US 6,315,763 B1
(45) Date of Patent: Nov. 13, 2001

(54) TAMPON

(75) Inventors: Mark Albright, West Brookfield; Fiona Taylor, Palmer, both of MA (US); Nigel Sanger, Rowlands Castle (GB); Carolyn Whyte, Lexington, MA (US)

(73) Assignee: Tambrands, Inc., Cincinnati, OH (US)

( * ) Notice: Subject to any disclaimer, the term of this patent is extended or adjusted under 35 U.S.C. 154(b) by 0 days.

(21) Appl. No.: 08/967,976

(22) Filed: Nov. 12, 1997

Related U.S. Application Data

(63) Continuation of application No. 08/834,620, filed on Apr. 14, 1997, now abandoned.

(51) Int. Cl.⁷ ................................................. A61F 13/15
(52) U.S. Cl. ...................................... 604/385.18; 604/904
(58) Field of Search ............................... 604/11–18, 363, 604/358, 904

(56) References Cited

U.S. PATENT DOCUMENTS

| | | | |
|---|---|---|---|
| 2,340,311 | * 2/1944 | Donovan | 604/363 |
| 2,440,141 | * 4/1948 | Donovan | 604/363 |
| 3,340,874 | * 9/1967 | Burgeni | 604/904 |
| 3,523,535 | * 8/1970 | Croon | 604/904 |
| 4,211,225 | * 7/1980 | Sibalis | 604/904 |
| 4,226,237 | * 10/1980 | Levesque | 604/904 |
| 4,276,338 | 6/1981 | Ludwa et al. . | |
| 4,305,391 | 12/1981 | Jackson . | |
| 4,335,722 | * 6/1982 | Jackson | 128/285 |

FOREIGN PATENT DOCUMENTS 0 685 215 A1   5/1995   (EP) .

* cited by examiner

Primary Examiner—Dennis Ruhl
(74) Attorney, Agent, or Firm—Theodore P. Cummings; Matthew P. Fitzpatrick; Kevin C. Johnson

(57) ABSTRACT

A tampon is provided with a permeable or soluble barrier layer interposed between an absorbent core and an overwrap, allowing substantially complete, uniform wetting to be obtained even under light flow conditions. The barrier prevents immediate flow of fluid into the core, allowing time for fluid to be carried by the overwrap around the outer surface of the tampon, prior to being drawn into the absorbent core.

12 Claims, 1 Drawing Sheet

TAMPON

CROSS REFERENCE TO RELATED APPLICATIONS

This is a continuation of application Ser. No. 08/834,620, filed on Apr. 14, 1997, abandoned.

BACKGROUND OF THE INVENTION

The present invention relates to tampons.

Tampons may be formed from two types of pledgets, a rolled pledget, formed by providing a section of specific length of an absorbent material, e.g. a nonwoven web, having a width corresponding approximately to the length of the tampon, and winding or rolling the section upon itself to form a pledget, or non-rolled pledgets, formed by providing a batt of absorbent material having a width corresponding approximately to the length of the tampon. In both cases, the pledget is compressed radially to form a finished tampon. The term "pledget", as used herein, refers to both rolled and non-rolled pledgets.

Tampons are often provided with an overwrap, i.e. an outer covering of a liquid permeable material, for example a thermoplastic nonwoven, to improve the smoothness of the tampon surface, reducing insertion and withdrawal forces, and to prevent fibers of the nonwoven from being detached ("fiber fluff-off") during insertion and withdrawal.

One problem common to both types of tampons is uneven or incomplete wetting of the surface of the tampon, particularly during conditions of light menstrual flow. Incomplete or uneven wetting tends to result in drying of the vaginal epithelium, in part due to the rapid initial uptake of vaginal secretions into dry areas of the tampon to equilibrate the relative moisture contents of these areas of the tampon and the vaginal epithelium. Drying of the vaginal epithelium may cause discomfort, because the dry vaginal wall will tend to resist withdrawal of the tampon, potentially causing epithelial abrasions. This phenomenon tends to be disconcerting to tampon users, and can make tampon withdrawal difficult and uncomfortable.

SUMMARY OF THE INVENTION

The inventors have found that by providing a tampon with a semi-permeable or soluble barrier layer interposed between an absorbent core and an overwrap, substantially uniform wetting around the outer surface of the tampon can be obtained even under light menstrual fluid conditions, e.g., a flow of less than one gram of fluid, provided there is a minimal volume of fluid sufficient to wet substantially the entire outer surface. The barrier prevents immediate flow of fluid into the core, allowing time for fluid to be transported via capillary action within the overwrap around the outer surface of the tampon, prior to being drawn into the absorbent core. The overwrap transports the fluid around the outer surface of the tampon to improve evenness of wetting, without significantly reducing the absorbent capacity of the tampon.

The invention features a tampon including an absorbent core, an insertion end dimensioned for insertion into a body cavity, a withdrawal end, a withdrawal cord extending from to the withdrawal end, and a body extending between the insertion end and the withdrawal end. The tampon further includes an overwrap covering at least a portion of the absorbent core, and a barrier layer interposed between the overwrap and surface of the absorbent core. Preferably, the absorbent core comprises a rolled, radially compressed pledget. The overwrap may cover the entire absorbent core, or may cover only a portion of the absorbent core, e.g., the overwrap may cover the body but be open at the insertion end and/or withdrawal end. The barrier layer preferably covers the entire surface of the absorbent core, but in some embodiments may be open at the insertion end and/or withdrawal end. The barrier layer preferably covers at least the area of the tampon surface that contacts the vaginal wall during use. If the barrier layer is open at the insertion end, it is preferred that the insertion end of the tampon be covered by, or coated with, a second barrier material, to prevent fluid from being drawn into the core through the insertion end prior to substantially complete wetting of the outer surface of the tampon.

In a first embodiment, the barrier layer is semipermeable to initially retard and then eventually allow flow of menstrual fluid through the barrier layer once the outer surface of the tampon has been wetted. The barrier layer may be a porous, perforated or slit film, or may be a fluid-permeable membrane. A preferred barrier layer is a slit cellophane film. Preferably the barrier layer includes about 1 to 10% fluid-permeable area. It is preferred that the orientation of the slits of the slit film be selected from the group consisting of: parallel to the longitudinal axis of the tampon (the axis extending between the insertion and withdrawal ends of the body), perpendicular to the longitudinal axis of the tampon, and diagonal to the longitudinal axis of the tampon.

In a second embodiment, the barrier layer is initially fluid impermeable but is highly water soluble. When the tampon is inserted fluid is momentarily prevented by the barrier layer from being drawn into the absorbent core, allowing the fluid to instead travel around and wet the surface of the tampon, carried by the overwrap. Shortly after insertion, the barrier layer dissolves in the menstrual fluid, allowing fluid to flow into the absorbent core. Preferred impermeable, water soluble barrier layers include but are not limited to films of polyvinyl alcohol, polyvinyl pyrrolidone, polyethylene oxide and polyethylene glycol. Preferably, the barrier layer has a solubility rate i.e., the (time required for a fluid to pass through the film) of from about 1 to 30 min. in physiological saline solution (1%).

The porosity and/or solubility of the barrier layer is selected to allow the surface of the tampon to be substantially completely wetted even under conditions of low menstrual flow, while also allowing fluid to flow into the absorbent core almost immediately after fluid contact with the overwrap.

Preferably, the compressed pledget has a smooth, cylindrical outer surface, rather than a fluted shape as is conventional for digital tampons. The smooth surface provides a continuous uninterrupted path for fluid flow over the surface of the pledget.

Other features of the invention will be apparent from the following description of preferred embodiments, from the claims, and from the drawings.

BRIEF DESCRIPTION OF THE DRAWINGS

FIG. 2 is a cross-sectional side view of the tampon of FIG. 1, taken along line 1a—1a.

DESCRIPTION OF THE PREFERRED EMBODIMENTS

Figure 1:
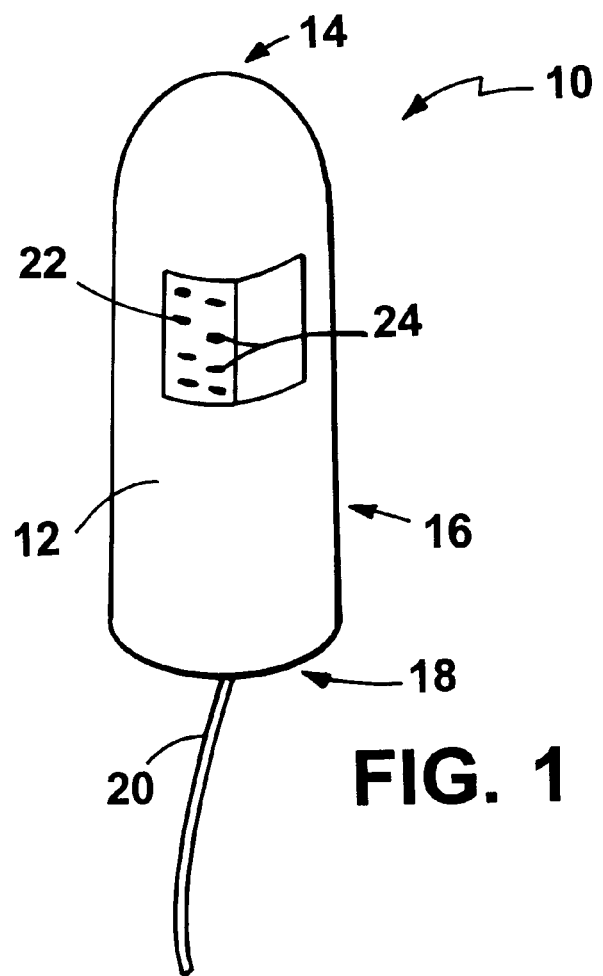
FIG. 1 is a side view of a tampon according to one embodiment of the invention, with a portion of the overwrap cut away to show the underlying barrier layer.
Figure 2:
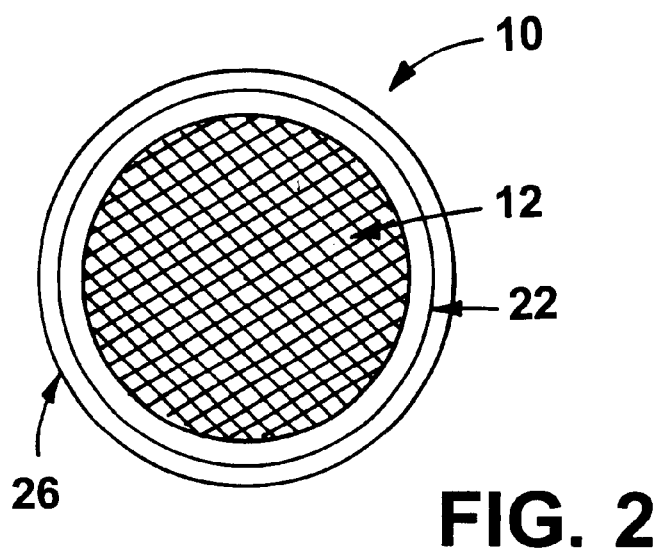

Referring to FIGS. 1 and 2 a preferred tampon 10 includes a pledget 12 having an insertion end 14, a body 16, a withdrawal end 18, and a withdrawal cord 20. Tampon 10 further includes a barrier layer 22 adjacent the surface of pledget 12, and an overwrap 26 surrounding the barrier layer 22. Preferably, the barrier layer has a thickness of from about 10 to 50 microns, more preferably from about 18 to 25 microns. In the embodiment shown in FIG. 1, the barrier layer is a cellophane film having a plurality of substantially parallel slits 24. Instead of slits, the barrier layer can have any desired pattern of pores, perforations or other openings.

Alternatively, instead of the slit cellophane film, barrier layer 22 can be another type of semi-permeable, porous, perforated or slit material which is either soluble or insoluble in menstrual fluid. Moreover, barrier layer 22 can be any suitable impermeable material that is sufficiently soluble in menstrual fluid to allow it to dissolve at a controlled rate upon contact with menstrual fluid. Suitable water-soluble films include polyvinyl pyrrollidone polyethylene oxide, polyethylene glycol, and polyvinyl alcohol. Other suitable barrier layers include coatings of synthetic non-paraffin waxes.

Suitable overwraps are hydrophilic permeable sheet materials that will wick or draw menstrual fluid over the surface of the pledget during the time period prior to absorption of the fluid into the core, i.e., the time prior to dissolution of the barrier layer or passage of the fluid through the slits or perforations in the barrier layer. Suitable overwrap materials include, but are not limited to, chemically bonded rayon, nonwovens, thermobonded nonwovens, nonwovens with hydrophilic treatments, spunbonded webs, and hydroentangled webs. Preferred fibers for use in the overwrap include but are not limited to chemically bonded rayon, polypropylene and bicomponent fibers treated with hydrophilic treatments. The preferred basis weight of the overwrap is from about 15 to 30 g/m$^2$, more preferably 30 g/m$^2$.

Preferably, the barrier layer covers at least the area of the tampon surface that contacts the vaginal wall during use. The barrier layer may be open at the insertion end of the tampon. When this is the case, the insertion end of the tampon is preferably coated with a separate barrier layer or material, e.g., a coating of a water-soluble polymer such as a synthetic wax. A preferred coating is polyethylene glycol, more preferably a grade of polyethylene glycol having a molecular weight of from about 20,000 to 100,000.

Any conventional absorbent material is suitable for use in the tampon of the invention. Preferred absorbent materials are selected from the group consisting of cellulosic fibers, cotton fibers, rayon fibers and blends thereof. Most preferred are blends of cotton and rayon fibers.

Preferably, the compressed pledget has a smooth, rather than fluted, outer surface as shown in FIG. 1. The smooth outer surface facilitates movement of fluid over the surface of the tampon.

For ease of manufacturing, it is preferred that the overwrap and the barrier layer be laminated together to form a single laminated sheet which can applied to the absorbent core in a single step.

Other embodiments are within the claims. For example, while the slits of the slit film are shown as being substantially parallel and straight, they could have any desired shape and orientation, e.g., they could be L-shaped, S-shaped, or straight but not arranged parallel to each other.

What is claimed is:

1. A tampon comprising:
   an absorbent core, the absorbent core comprising a rolled, radially compressed pledget,
   an insertion end dimensioned for insertion into a body cavity, a withdrawal end, a withdrawal cord attached to the withdrawal end, and a body extending between the insertion end and the withdrawal end,
   an overwrap having an overwrap surface covering at least a portion of the absorbent core, and
   a first barrier layer interposed between the overwrap surface and the surface of the absorbent core, wherein said barrier layer is capable of retarding flow of fluids into the absorbent core to provide substantially uniform wetting about the overwrap surface prior to migration of fluids into the absorbent core, the barrier layer comprising a slit cellophane film to accomplish the regarding flow of fluids into the absorbent core.

2. The tampon of claim 1 wherein the tampon has a longitudinal axis extending between the insertion and withdrawal ends, and the slit cellophane film includes a plurality of substantially parallel slits having an orientation selected from the group consisting of: slits parallel to the longitudinal axis of the tampon, slits perpendicular to the longitudinal axis of the tampon, and slits diagonal to the longitudinal axis of the tampon.

3. The tampon of claim 1 wherein the barrier layer includes from about 1 to about 10% fluid permeable area.

4. The tampon of claim 1 wherein the barrier layer has a thickness of from about 10 to 50 microns.

5. The tampon of claim 4 wherein the barrier layer has a thickness of from about 18 to 25 microns.

6. The tampon of claim 1 wherein the overwrap is of a hydrophilic nonwoven.

7. The tampon of claim 1 wherein the tampon has a smooth, cylindrical outer surface to provide a continuous path for fluid flow over the surface of the tampon.

8. The tampon of claim 1 wherein said barrier layer and said overwrap are laminated together to form a single laminated sheet.

9. A tampon comprising:
   an absorbent core,
   an insertion end dimensioned for insertion into a body cavity, a withdrawal end, a withdrawal cord attached to the withdrawal end, and a body extending between the insertion end and the withdrawal end,
   an overwrap having an overwrap surface covering at least a portion of the absorbent core,
   a first barrier layer interposed between the overwrap surface and the surface of the absorbent core, wherein said barrier layer is capable of retarding flow of fluids into the absorbent core to provide substantially uniform wetting about the overwrap surface prior to migration of fluids into the absorbent core, said first barrier layer covers a first surface along the body of the absorbent core, the barrier layer comprising a slit cellophane film to accomplish the retarding flow of fluids into the absorbent core and,
   a second barrier layer interposed between the overwrap surface and the absorbent core covering the insertion end of the absorbent core wherein said second barrier layer prevents fluid from being drawn into the core thorough the insertion end prior to substantially complete wetting of the surface of the tampon.

10. The tampon of claim 9 wherein the second barrier layer comprises a water soluble polymer.

11. The tampon of claim 10 wherein said water soluble polymer is a polyethylene glycol.

12. The tampon of claim 11 wherein said polyethylene glycol has a molecular weight of from about 20,000 to 100,000.

* * * * *